(12) United States Patent
Suzuki et al.

(10) Patent No.: US 11,207,493 B2
(45) Date of Patent: Dec. 28, 2021

(54) MEDICAL ELONGATED BODY

(71) Applicant: TERUMO KABUSHIKI KAISHA, Tokyo (JP)

(72) Inventors: Kenta Suzuki, Fujinomiya (JP); Akihiko Tarunaga, Mishima (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 272 days.

(21) Appl. No.: 16/046,186

(22) Filed: Jul. 26, 2018

(65) Prior Publication Data

US 2018/0344971 A1 Dec. 6, 2018

Related U.S. Application Data

(63) Continuation of application No. PCT/JP2017/010935, filed on Mar. 17, 2017.

(30) Foreign Application Priority Data

Mar. 22, 2016 (JP) .............................. JP2016-056649

(51) Int. Cl.
*A61M 25/00* (2006.01)
*A61M 5/00* (2006.01)
(Continued)

(52) U.S. Cl.
CPC ........ *A61M 25/003* (2013.01); *A61M 25/005* (2013.01); *A61M 25/01* (2013.01);
(Continued)

(58) Field of Classification Search
CPC ............ A61M 25/003; A61M 25/0175; A61M 25/01; A61M 25/0062; A61M 25/0052;
(Continued)

(56) References Cited

U.S. PATENT DOCUMENTS 5,156,594 A * 10/1992 Keith ................ A61M 25/0662
604/103.09
5,295,962 A 3/1994 Crocker et al.
(Continued)

FOREIGN PATENT DOCUMENTS

CN 1473057 A 2/2004
CN 103561796 A 2/2014
(Continued)

OTHER PUBLICATIONS

English translation of the Written Opinion of the International Searching Authority and Search Report dated May 30, 2017 in International Application No. PCT/JP2017/010935.
(Continued)

*Primary Examiner* — Emily L Schmidt
*Assistant Examiner* — Leah J Swanson
(74) *Attorney, Agent, or Firm* — Buchanan Ingersoll & Rooney PC

(57) ABSTRACT

A medical elongated body is disclosed, which includes a shaft having a lumen through which a contrast agent can flow; and a tubular structure portion which is provided at a distal portion of the shaft and has an insertion hole. The tubular structure portion includes an inner tube fixed to the distal portion of the shaft; an outer tube which is disposed radially outward of the inner tube and is liquid-tightly fixed to the distal portion of the shaft and a proximal portion of the inner tube; a space portion communicating with the lumen of the shaft between the inner tube and the outer tube, and an opening portion through which a contrast agent flows from the lumen into the space portion flows out.

20 Claims, 7 Drawing Sheets

(51) Int. Cl.
*A61M 25/06* (2006.01)
*A61M 25/01* (2006.01)
*A61F 2/958* (2013.01)

(52) U.S. Cl.
CPC ......... *A61M 25/0662* (2013.01); *A61F 2/958* (2013.01); *A61M 5/007* (2013.01); *A61M 25/007* (2013.01); *A61M 25/0052* (2013.01); *A61M 2025/0004* (2013.01); *A61M 2025/0039* (2013.01); *A61M 2025/0183* (2013.01)

(58) Field of Classification Search
CPC .. A61M 2025/0031; A61M 2025/0183; A61M 25/0067; A61M 25/0068; A61M 25/0069; A61M 25/007; A61M 2005/105; A61M 2005/0034; A61M 2005/0039; A61M 2005/0004

See application file for complete search history.

(56) References Cited

U.S. PATENT DOCUMENTS

| | | | |
|---|---|---|---|
| 5,562,620 A | 10/1996 | Klein et al. | |
| 6,146,373 A | 11/2000 | Cragg et al. | |
| 6,503,223 B1* | 1/2003 | Sekido | A61M 25/003 604/264 |
| 6,729,334 B1* | 5/2004 | Baran | B67D 7/06 128/207.14 |
| 9,199,058 B2 | 12/2015 | Lentz | |
| 2004/0015138 A1* | 1/2004 | Currier | A61M 25/007 604/264 |
| 2004/0116957 A1 | 6/2004 | Nishide et al. | |
| 2005/0288632 A1* | 12/2005 | Willard | A61M 25/10 604/103.01 |
| 2008/0255447 A1 | 10/2008 | Bourang et al. | |
| 2012/0065579 A1* | 3/2012 | Cully | A61M 25/0045 604/26 |
| 2013/0116701 A1 | 5/2013 | Wang et al. | |
| 2015/0265805 A1 | 9/2015 | Vakili et al. | |
| 2016/0082225 A1 | 3/2016 | Kobayashi | |

FOREIGN PATENT DOCUMENTS

| | | | |
|---|---|---|---|
| CN | 105142709 A | 12/2015 | |
| JP | 2001520085 A | 10/2001 | |
| JP | 2011135989 A | 7/2011 | |
| JP | 2013128602 A | 7/2013 | |
| WO | WO-9732626 A2 * | 9/1997 | .......... A61M 25/104 |
| WO | 2012/137177 A1 | 10/2012 | |
| WO | 2014/152191 A1 | 9/2014 | |
| WO | 2015/117025 A1 | 8/2015 | |

OTHER PUBLICATIONS

The extended European Search Report dated Dec. 4, 2019, by the European Patent Office in corresponding European Patent Application No. 17770164.6-1132. (5 pages).

Office Action (The First Office Action) dated Apr. 26, 2020, by the State Intellectual Property Office of People's Republic of China in corresponding Chinese Patent Application No. 201780012737.7 and an English Translation of the Office Action. (16 pages).

International Search Report (PCT/ISA/210) dated May 30, 2017, by the Japanese Patent Office as the International Searching Authority for International Application No. PCT/JP2017/010935.

Written Opinion (PCT/ISA/237) dated May 30, 2017, by the Japanese Patent Office as the International Searching Authority for International Application No. PCT/JP2017/010935.

* cited by examiner

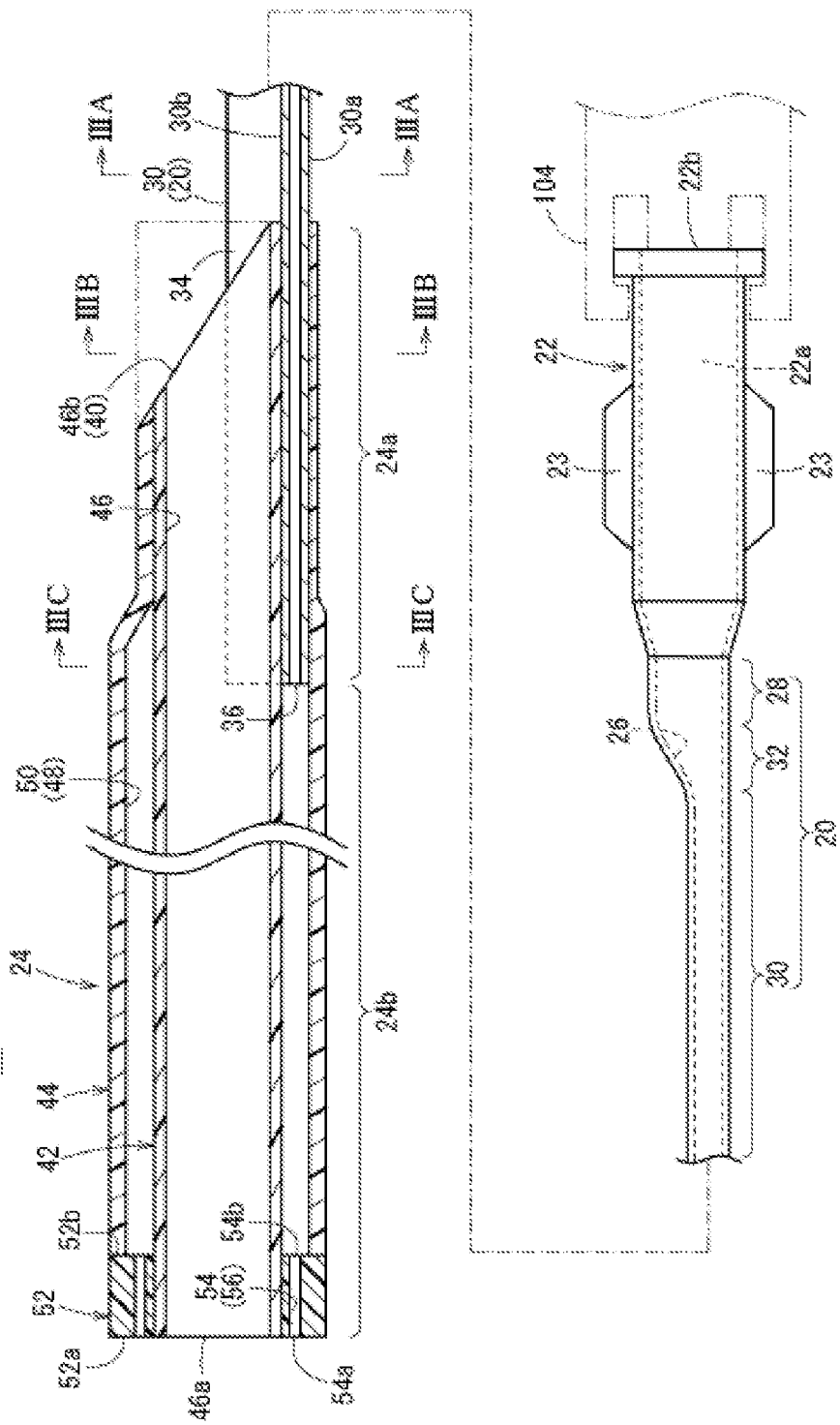

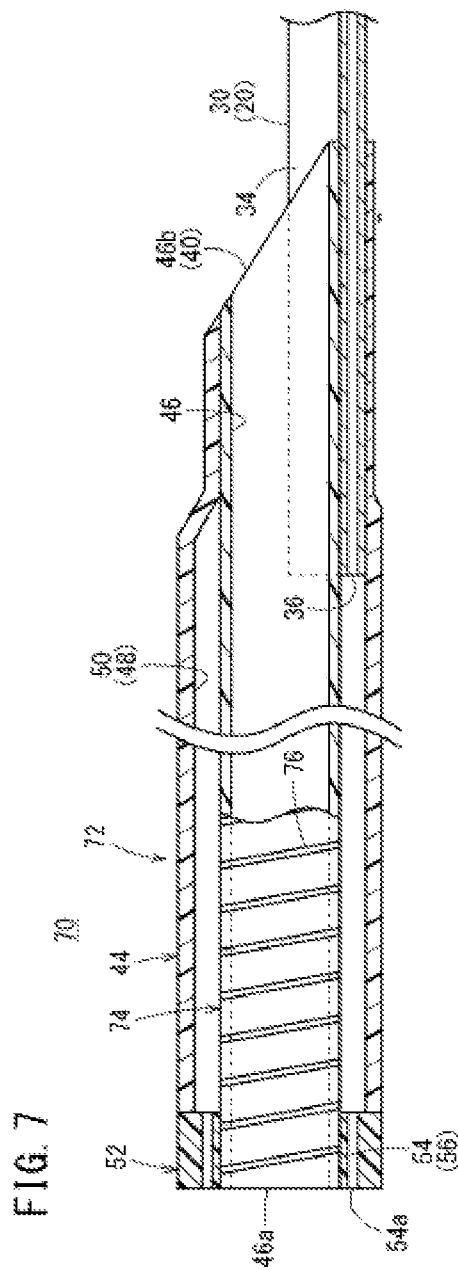

MEDICAL ELONGATED BODY

CROSS-REFERENCES TO RELATED APPLICATIONS

This application is a continuation of International Application No. PCT/JP2017/010935 filed on Mar. 17, 2017, which claims priority to Japanese Application No. 2016-056649 filed on Mar. 22, 2016, the entire contents of both of which is incorporated herein by reference.

TECHNICAL FIELD

The present disclosure generally relates to a medical elongated body used in an interventional manipulation, for example, for assisting advancement of a medical device.

BACKGROUND ART

In a case of intravascular treatment, an operator advances a guiding catheter along a guide wire, which has been advanced in a blood vessel, and delivers a medical device for intervention through the guiding catheter. After advancing (or sending out) the medical device from the guiding catheter, the medical device is advanced to a lesion area to treat the lesion area. In this type of manipulation, in a case where the distance of advancing the medical device from the guiding catheter is relative long, the medical device receives resistance, for example, in sites that are largely stenosed, bent, or meandered within a blood vessel. Therefore, it can become difficult to advance the medical device.

In such a case, the operator disposes a guiding catheter (parent catheter) in a desired site within a blood vessel. Then, the operator sends out a medical elongated body (child catheter) from a distal end of the guiding catheter and advances the medical elongated body to the proximity of a stenosed site (lesion area) (refer to JP-A-2011-135989). Accordingly, the medical elongated body can support the medical device at the distal end of the guiding catheter to support the advancement of medical device. In particular, since the medical elongated body disclosed in JP-A-2011-135989 is a rapid exchange type catheter having a wire and an insertion tube at a distal portion of the wire, the operator can insert the medical device into the tube and can rather easily move the medical elongated body with respect to the guiding catheter.

SUMMARY

However, during the intravascular treatment, a contrast agent (for example, a fluid) may flow out into the blood vessel through a lumen of the guiding catheter and radiography in the vicinity of the lesion area can be performed in order to check the condition, such as the position of the lesion area, in the blood vessel. However, in a case of using a rapid exchange type medical elongated body, the contrast agent injected from a hand-side (i.e., proximal side) of the guiding catheter is delivered to the distal side of the guiding catheter through the lumen of the guiding catheter, which is larger than an outer shape of the medical elongated body. For this reason, during imaging of the vicinity of the lesion area by discharging the contrast agent to the distal side of the medical elongated body, the operator generally uses a large amount of the contrast agent.

A medical elongated body is disclosed, which is capable of reliably discharging a fluid from the distal side of a rapid exchange type medical elongated body and thereby reducing the amount of the fluid used.

A medical elongated body according to the present disclosure includes: a shaft having a lumen through which a fluid can flow; and a tubular structure portion which is provided at a distal portion of the shaft and has an insertion hole, in which the tubular structure portion includes a first tube body which has the insertion hole and is fixed to the distal portion of the shaft, a second tube body which is disposed radially outward of the first tube body and is liquid-tightly fixed to the distal portion of the shaft and a proximal portion of the first tube body, a space portion which is provided between the first tube body and the second tube body and communicates with the lumen of the shaft, and an opening portion which is positioned at a distal portion of the tubular structure portion and through which a fluid flows from the lumen of the shaft into the space portion flows out of the tubular structure portion.

According to the above description, the medical elongated body has a structure in which the lumen of the shaft and the space portion and the opening portion of the tubular structure portion communicate with each other. In addition, the proximal portion of the first tube body forming the space portion is liquid-tightly fixed to the second tube body. For this reason, the medical elongated body can cause a fluid injected from a proximal side of the shaft to reliably flow from the opening portion of the tubular structure portion. In accordance with an exemplary embodiment, for example, since the second tube body is liquid-tightly fixed to the shaft and the first tube body, the fluid flowing into the space portion from the lumen of the shaft smoothly moves the space portion in a distal direction without leakage to the outside of the shaft. Accordingly, the medical elongated body discharges a contrast agent (fluid) from the distal side of the medical elongated body, and therefore, the intravascular condition (for example, a lesion area on the distal side of the medical elongated body) can be clearly recognized during X-ray photographing. In addition, since the medical elongated body can reliably cause the contrast agent flow to the distal side of the medical elongated body, the amount of the contrast agent used can be reduced, for example, where the contrast agent is a fluid.

In addition, it can be preferable that the shaft has, for example, on the distal side of the shaft, a groove portion formed by recessing an outer surface of the shaft toward the lumen of the shaft and a cross-sectional area of the lumen of the shaft at the distal portion in a cross-section orthogonal to an axial center of the shaft is smaller than that of the lumen of the shaft at a proximal portion in a cross-section orthogonal to the axial center of the shaft.

In accordance with an aspect, since the groove portion is provided on the distal side of the shaft in this manner, the medical elongated body can widen the space on the proximal side of the tubular structure portion through which a medical device is to be inserted. Accordingly, when the medical device is inserted toward the tubular structure portion, the medical elongated body can help suppress the medical device from being caught by the shaft due to the groove portion. Accordingly, an operator can relatively smoothly insert the medical device into the insertion hole of the tubular structure portion of the medical elongated body. In addition, since the cross-sectional area of the lumen of the shaft at the distal portion is smaller than that of the lumen of the shaft at the proximal portion, the flow speed of a fluid can be increased from the proximal side of the shaft to the distal side of the shaft when the fluid flows in the lumen of the shaft. Accordingly, the medical elongated body can cause a highly viscous fluid such as a contrast agent to flow relatively smoothly. In addition, since the medical elongated body includes the groove portion on the outer surface of the shaft, the medical device can follow the groove portion such that the medical device slides relatively smoothly.

In accordance with an exemplary embodiment, it can be preferable that the cross-sectional area in a cross-section orthogonal to an axial center of the lumen of the shaft decreases from the proximal side of the lumen of the shaft toward the distal side of the shaft. Accordingly, a highly viscous fluid such as a contrast agent can flow relatively smoothly in the lumen of the medical elongated body. In addition, it can be preferable, for example, that the cross-sectional area in a cross-section orthogonal to an axial center of an outer shape of the shaft decreases from the proximal side of the outer shape of the shaft toward the distal side of the shaft. Accordingly, an operator can smoothly insert the medical device into the insertion hole of the tubular structure portion of the medical elongated body. In addition, it can be preferable, for example, that the cross-sectional area in the cross-section orthogonal to the axial center of the outer shape of the shaft decreases from the proximal side of the shaft toward the distal side of the shaft and the circumferential length of the outer circumference of the cross-section orthogonal to the axial center of the shaft decreases from the proximal side of the shaft toward the distal side of the shaft. Accordingly, the shaft becomes flexible from the proximal side of the shaft toward the distal side of the shaft. Therefore, the medical elongated body can be suitably operated in a relatively thin and curved blood vessel.

In addition, it can be preferable, for example, that the lumen of the shaft at the distal portion in the cross-section orthogonal to the axial center of the shaft is formed in a U-shape.

Since the lumen of the shaft at the distal portion is formed in a U-shape in this manner, the medical elongated body can secure the lumen of the shaft widely (i.e., an area of the lumen of the shaft can be kept or maintained with a relatively large area) at a joint portion between the shaft and the tubular structure portion. Accordingly, the operator can cause a contrast agent smoothly flow from a hand-side (proximal side) of the shaft to the opening portion of the tubular structure portion through the lumen of the shaft and the space portion of the tubular structure portion. In addition, since the lumen of the shaft at the distal portion is formed in a U-shape, the medical elongated body can widen the space on the proximal side of the tubular structure portion through which a medical device is to be inserted. Accordingly, an operator can smoothly insert the medical device into the insertion hole of the tubular structure portion of the medical elongated body.

In addition, it can be preferable, for example, that the first tube body is fixed to the groove portion of the shaft.

In accordance with an exemplary embodiment, since the first tube body can be fixed to the groove portion of the shaft, the first tube body can be firmly fixed to the groove portion of the shaft. For this reason, in the medical elongated body, the joining between the tubular structure portion and the shaft can be enhanced, and therefore, a risk of rupture of the tubular structure portion and the shaft can be suppressed.

In addition, it can be preferable, for example, that a cross-sectional area of the opening portion in a cross-section orthogonal to an axial center of the shaft is smaller than that of the lumen of the shaft at the distal portion in a cross-section orthogonal to the axial center of the shaft.

Since the cross-sectional area of the opening portion of the medical elongated body can be made to be smaller than that of the lumen of the shaft at the distal portion, it is possible to smoothly discharge a fluid flowing from the lumen of the shaft. Accordingly, the medical elongated body can make a highly viscous fluid such as a contrast agent smoothly flow toward the opening portion.

In addition, it can be preferable, for example, that the tubular structure portion has a distal tip, the distal tip being made of a material more flexible than that of the second tube body, at the distal portion, and the distal tip liquid-tightly fixes the first tube body and the second tube body at the distal side of the tubular structure portion while forming the opening portion.

Since the tubular structure portion includes the flexible distal tip as described, damage of the body lumen due to the distal portion of the medical elongated body can be suppressed.

In addition, at least one of an outer surface of the first tube body and an inner surface of the second tube body may be provided with a reinforcement body for reinforcing the tubular structure portion.

Since the medical elongated body has the reinforcement body in at least one of the first tube body and the second tube body as described, an extending state of the tubular structure portion can be stably secured. In addition, since a fluid flowing in the space portion is stirred by the reinforcement body in the medical elongated body, the fluid can be spread in the circumferential direction of the space portion of the tubular structure portion. Since the reinforcement body is provided in a spiral shape on the outer surface of the first tube body or the inner surface of the second tube body in the medical elongated body, the fluid can be guided so as to flow while rotating in the space portion in the circumferential direction and to cause the fluid more uniformly flow out from the circumferential direction of the opening portion.

In accordance with an exemplary embodiment, a medical elongated body, the medical elongated body comprising: a shaft having a lumen through which a fluid can flow; and a tubular structure portion arranged at a distal portion of the shaft, the tubular structure including: an inner tubular body configured to be fixed to the distal portion of the shaft; an outer tubular body radially disposed outward of the inner tubular body and is liquid-tightly fixed to the distal portion of the shaft and a proximal portion of the inner tubular body; an annular space provided between the first tube body and the second tube body and in fluid communication with the lumen of the shaft; and a distal tip positioned at a distal portion of the tubular structure portion and through which the fluid flowing from the lumen of the shaft is discharged into a body lumen from the annular space.

In accordance with another exemplary embodiment, a method for discharging a contrast agent into a body lumen, the method comprising: inserting a medical elongated body into the body lumen, the medical elongated body including a shaft having a lumen through which the contrast agent can flow, and a tubular structure portion which is provided at a distal portion of the shaft and has an insertion hole, wherein the tubular structure portion includes: a first tube body which has the insertion hole and is fixed to the distal portion of the shaft; a second tube body which is disposed radially outward of the first tube body and is liquid-tightly fixed to the distal portion of the shaft and a proximal portion of the first tube body; a space portion which is provided between the first tube body and the second tube body and communicates with the lumen of the shaft; and an opening portion which is positioned at a distal portion of the tubular structure portion; and discharging the contrast agent through the opening portion into the body lumen.

According to the present disclosure, the contrast agent can be reliably discharged from the distal side of the medical elongated body in the rapid exchange type medical elongated body, and therefore, it is possible to simply image the body lumen such as a blood vessel. In addition, the medical elongated body of the present invention can reduce the amount of contrast agent used.

BRIEF DESCRIPTION OF THE DRAWINGS

FIG. 2 is a cross-sectional side view of the medical elongated body of FIG. 1.

FIG. 7 is a cross-sectional side view showing a tubular structure portion of a medical elongated body according to another application example.

DETAILED DESCRIPTION

Hereinafter, a medical elongated body according to the present disclosure will be described in detail with reference to the accompanying drawings using a suitable embodiment.

Figure 5A:
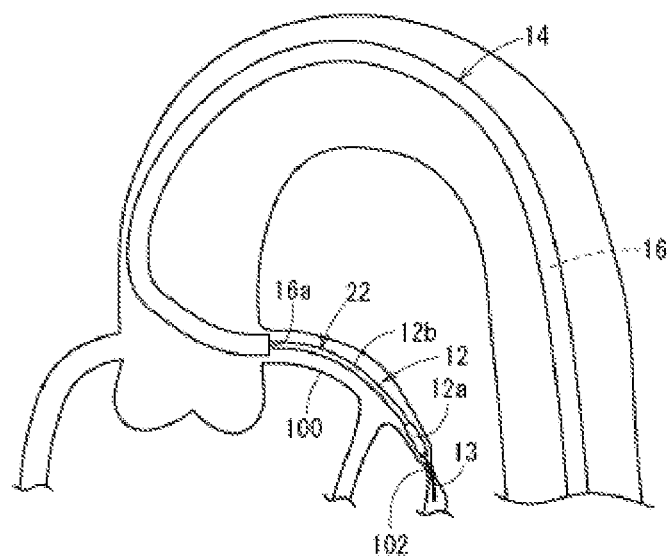
FIG. 5A is a first explanatory view showing a procedure of percutaneous coronary intervention.

A medical elongated body 10 according to the present embodiment is formed as a device for supporting a medical device 12 (for example, a balloon catheter or a stent delivery device: refer to FIG. 5A) in order to pass the medical device 12 through a lesion area during treatment or diagnosis of the inside of the body lumen such as a blood vessel. Accordingly, the medical elongated body will also be called a support catheter 10 below. Examples of the body lumen in which the support catheter 10 can be used include various organs such as the bile duct, the trachea, the esophagus, the urethra, the nasal cavity, or other organs in addition to blood vessels.

Figure 1:
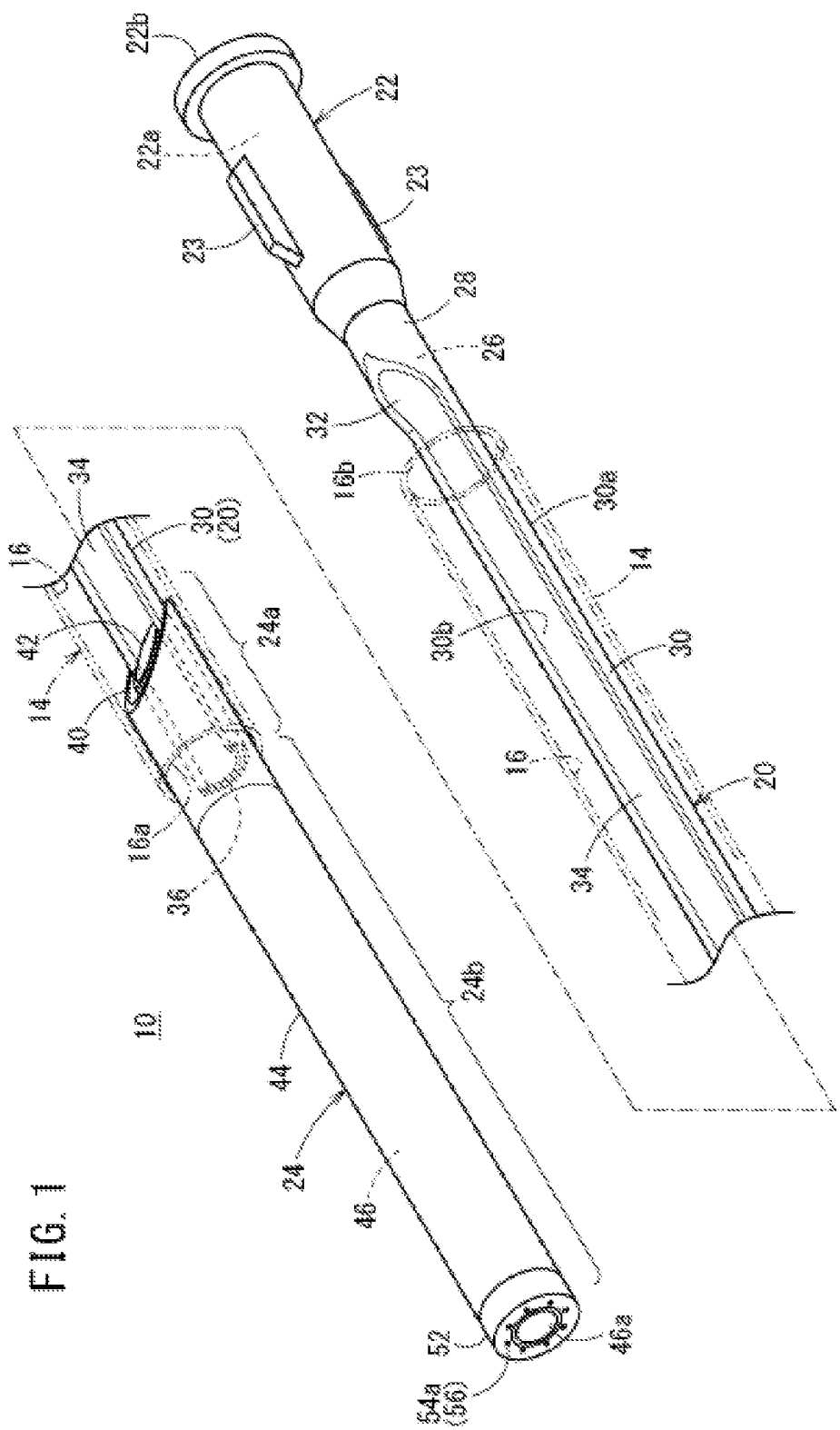
FIG. 1 is a perspective view showing an overall configuration of a medical elongated body according to an embodiment of the present invention.

In addition, as shown in FIG. 1, the support catheter 10 is advanced from a distal end of a guiding catheter 14 through the inside of the guiding catheter 14 and supports the medical device 12 within a blood vessel on a more distal side than the guiding catheter 14. That is, the support catheter 10 can also be referred to as a child catheter, which is inserted and guided into the guiding catheter 14, which is a parent catheter.

The guiding catheter 14 is not particularly limited, and a pipe body internally having a hollow portion 16 (lumen) which has an outer diameter that can be inserted into the body lumen to be treated and wherein the medical device 12 for intervention can be slid into the hollow portion 16 (lumen) of the guiding catheter 14. The hollow portion 16 communicates with a distal opening 16a of the guiding catheter 14 and a proximal opening 16b of a hub (not shown in the drawing) for fixing and supporting the guiding catheter 14. The support catheter 10 is formed in a size having an outer diameter to be movable in the hollow portion 16. Hereinafter, the configuration of the support catheter 10 according to the present embodiment will be specifically described.

As shown in FIGS. 1 and 2, the support catheter 10 includes a shaft 20, a hub 22 interlocked with and fixed to the proximal side of the shaft 20, and a tubular structure portion 24 interlocked with and fixed to the distal portion of the shaft 20. It can be preferable, for example, that the total length of the support catheter 10 is set appropriately (to be longer than the guiding catheter 14) according to the total length of the guiding catheter 14. For example, the total length of the support catheter may be about 200 mm to 5,000 mm.

In accordance with an exemplary embodiment, the support catheter 10 can be a rapid exchange type device, which can expose the medical device 12 and a guide wire 13 (i.e., a distal portion of the medical device 12 or guide wire 13) from a distal end of the support catheter 10, and a proximal portion of the medical device 12 (or guide wire 13) can be exposed at a midway portion (or middle position) of the support catheter 10 in an axial direction, using the tubular structure portion 24. Accordingly, the rapid exchange type support catheter 10 makes it possible to rather easily perform replacement of the guide wire 13 inserted through an insertion hole 46 of the tubular structure portion 24, and movement or replacement of the medical device 12.

The shaft 20 has a predetermined length in the axial direction and occupies most of the entire length of the support catheter 10. The shaft 20 is a hollow pipe body, and a lumen 26 through which a contrast agent (fluid) can flow is provided inside the shaft 20.

In addition, the shaft 20 has an outer shape different in the axial direction of the shaft 20. Specifically, the shaft 20 is formed in a round rod portion 28 having a circular shape on the proximal side of the shaft 20 in a cross-section orthogonal to an axial center of the shaft 20. In addition, a concave rod portion 30 having a semicircular arc shape is formed on a more distal side than the round rod portion 28 on a proximal side of the shaft 20. A transition portion 32 in which the outer shape of the shaft 20 gradually transitions is further provided at a boundary portion of the round rod portion 28 and the concave rod portion 30. The concave rod portion 30 extends between the transition portion 32 and the distal end of the shaft 20 and forms most of the shaft 20 in the axial direction. For example, the axial length of the concave rod portion 30 in the axial direction is set to be longer than the total length of the guiding catheter 14.

In accordance with an exemplary embodiment, for example, the concave rod portion 30 is formed such that approximately half of the outer surface of the concave rod portion 30 is a semicircular surface 30a with a large diameter of which the curvature is equal to that of the round rod portion 28 and the other half is a semicircular surface 30b with a small diameter which is recessed to the semicircular surface 30a with a large diameter in the cross-section orthogonal to the axial center of the shaft 20 (refer to FIG.

3A). In accordance with an exemplary embodiment, for example, the semicircular surface 30b with a small diameter forms a concave groove 34 (groove portion) extending along the axial direction of the recessed rod portion 30.

The cross-sectional shape of the concave rod portion 30 is not limited to a semicircle in the cross-section orthogonal to the axial center of the shaft 20, but may be an arc shape having the concave groove 34 shallower than a semicircle or may be a C-shape or a U-shape having the concave groove 34 deeper than a semicircle. In particular, in the case of the U-shaped concave groove 34, the shaft 20 can be passed through while deviation of the medical device 12 or the guide wire 13 is suppressed in the width direction of the shaft 20.

Figure 3A:
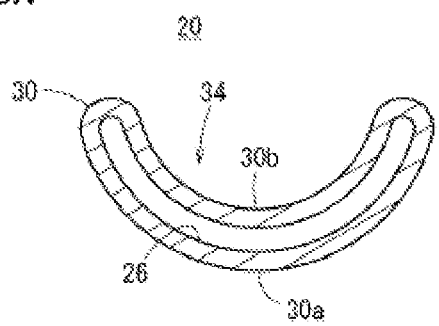
FIG. 3A is a cross-sectional view taken along line IIIA-IIIA of FIG. 2.

In accordance with an exemplary embodiment, the shape of the lumen 26 of the shaft 20 can be formed according to the outer shape of the shaft 20. That is, the lumen 26 is formed in a cross-sectional circular shape in the round rod portion 28 and is formed in a cross-sectional circular arc shape in the concave rod portion 30 (also refer to FIG. 3A). Although not shown in the drawing, in the transition portion 32, the shape of the lumen 26 gradually changes from the cross-sectional circular shape to the cross-sectional circular arc shape so as not to disturb flow of a fluid (for example, not to cause backflow or large turbulence). The lumen 26 of the concave rod portion 30 extends along the axial direction of the shaft 20 while the cross-sectional shape and the cross-sectional area are kept constant. An outlet port 36 which has a semicircular arc shape in front view in accordance with the outer shape of the concave rod portion 30 and communicates with the lumen 26 and through which a contrast agent can flow out is provided at the distal end of the shaft 20.

The cross-sectional area of the lumen (or channel) 26 of the concave rod portion 30 is set to be sufficiently smaller than that of the lumen 26 of the round rod portion 28. For example, the cross-sectional area of the lumen 26 of the concave rod portion 30 may be less than or equal to ⅕ of the cross-sectional area of the lumen 26 of the round rod portion 28. Accordingly, when a contrast agent is supplied from a hollow portion 22a of the hub 22 to the lumen 26 of the shaft 20, it is possible to accelerate the flow (increase the force) of the contrast agent in the lumen 26 of the concave rod portion 30 and to smoothly discharge the contrast agent into a blood vessel.

In addition, the transition portion 32 between the round rod portion 28 and the concave rod portion 30 is designed so as to be positioned in the vicinity of the distal end of the hub 22. Accordingly, even in a state in which the support catheter 10 is inserted into the guiding catheter 14 during the manipulation, the concave groove 34 is always exposed from the proximal end of the guiding catheter 14. When using the medical device 12, the support catheter 10 can cause the medical device to smoothly move relative to the inside of the hollow portion 16 of the guiding catheter 14 by making the medical device follow the inside of the concave groove 34 from the proximal end of the guiding catheter 14. In addition, the proximal portion of the round rod portion 28 is inserted into the hub 22 and fixed to the hub 22 using appropriate fixing means (through caulking, fusion, adhesion, and the like).

The materials from which the shaft 20 is fabricated are not particularly limited, but various metallic materials such as stainless steel and superelastic alloys such as Ni—Ti type alloy, Ni—Al type alloy, and Cu—Zn type alloy are preferably applied to the shaft 20. The outer peripheral surface of the shaft 20 may be coated with a coating that reduces sliding resistance with the medical device 12 including the medical device 12, the guide wire 13, and the guiding catheter 14. The concave rod portion 30 may be formed by crushing a tubular metal precursor having the same diameter as the round rod portion 28 through pressing or the like. The shaft 20 is not limited to the metallic materials, and a resin material may be applied thereto. For example, a resin material may be injected into a predetermined mold to be molded into the above-described shape.

In accordance with an exemplary embodiment, the hub 22 of the support catheter 10 firmly fixes the shaft 20 on the inside of the hub 22. For this reason, when an operator grips the hub 22 and operates the support catheter 10, the hub 22 transmits advancing/retreating operations, a rotation operation, or the like to the shaft 20 by the operator. The hub 22 can be formed to have a larger outer diameter than the shaft 20 so that the operator easily grasps the hub during the manipulation. In addition, the hub 22 has the hollow portion 22a inside the hub 22 and a proximal opening 22b communicating with the hollow portion 22a. The hollow portion 22a communicates with the lumen 26 of the shaft 20 on the distal side. For this reason, a fluid injected from the proximal opening 22b of the hub 22 flows into the lumen 26 of the shaft 20 through the hollow portion 22a.

A pair of wings (or protrusions) 23 can be further provided on the outer peripheral surface of the hub 22 for improving operability of the hub 22. For example, the wings (or protrusions) 23 may be provided to coincide with a portion where the concave groove 34 is formed in the circumferential direction of the shaft 20. Accordingly, the operator can rather easily recognize the position of the concave groove 34 in a state where the support catheter 10 is inserted into the body of a patient. In accordance with an exemplary embodiment, the pair of wings 23 may not be provided on the outer peripheral surface of the hub 22.

In accordance with an exemplary embodiment, the tubular structure portion 24 of the support catheter 10 can be fixed to a part (distal portion of the concave rod portion 30) of the shaft 20 to form a portion through which the medical device 12 or the guide wire 13 is inserted. The tubular structure portion 24 linearly extends from the distal end of the shaft 20 in the distal direction. A proximal end inclination portion 40 which is inclined obliquely with respect to the axial direction of the shaft 20 may be provided on the proximal side of the tubular structure portion 24 in order to facilitate insertion or removal of the medical device 12 or the guide wire 13 from the proximal side.

As shown in FIG. 2, the tubular structure portion 24 is formed in a dual lumen type catheter in which an inner tube 42 (first tube body) and an outer tube 44 (second tube body) are double-layered. In addition, the tubular structure portion 24 can be divided into a fixed region 24a which is fixed to the shaft 20 while overlapping with the shaft 20 and an extended region 24b extending from the fixed region 24a in the distal direction by a predetermined length, in the longitudinal direction of the tubular structure portion. In accordance with an exemplary embodiment, the fixed region 24a is composed of the shaft 20, the inner tube 42, and the outer tube 44, and the extended region 24b is composed of the inner tube 42 and the outer tube 44.

Figure 3B:
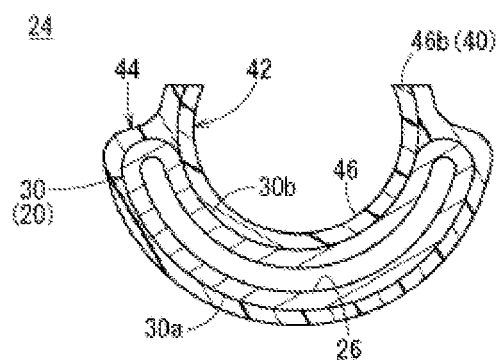
FIG. 3B is a cross-sectional view taken along line IIIB-IIIB of FIG. 2.
Figure 3C:
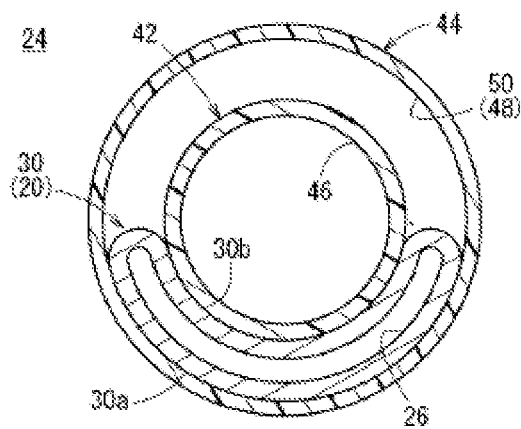
FIG. 3C is a cross-sectional view taken along line IIIC-IIIC of FIG. 2.

The inner tube 42 is formed in a hollow cylindrical shape extending linearly along the axial direction and internally has the insertion hole (or lumen) 46 through which the medical device 12 or the guide wire 13 can be inserted. As shown in FIGS. 3B and 3C, the curvature of the outer peripheral surface of the inner tube 42 is substantially equal to the curvature of the inner circumferential surface (semicircular surface 30b) of the concave groove 34 of the shaft 20. For this reason, the proximal-side outer peripheral surface of the inner tube 42 is fixed in a planar shape along the distal-side inner peripheral surface of the concave groove 34. Means for fixing the shaft 20 to the inner tube 42 is not particularly limited. For example, the shaft can be fixed to the inner tube so that the circumferential direction of the concave groove 34 is liquid-tightly blocked through fusion, adhesion, or the like.

As shown in FIG. 2, the insertion hole 46 penetrates through the inside of the inner tube 42 in the axial direction and communicates with a distal opening 46a provided at the distal end of the inner tube 42 and with a proximal opening 46b provided at the proximal end of the inner tube 42. The proximal opening 46b is inclined at a predetermined angle with respect to the axial center of the inner tube 42 according to the proximal end inclination portion 40 of the tubular structure portion 24. Accordingly, the insertion hole 46 extends in a groove shape at the position at which the proximal end inclination portion 40 is formed (also refer to FIG. 3B).

In accordance with an exemplary embodiment, it can be preferable, for example, that the inner tube 42 is formed to be more flexible than the shaft 20. The material from which the inner tube 42 is fabricated is not particularly limited, but examples of the material include polyolefin resins such as high density polyethylene, polypropylene, polybutene, vinyl chloride, and an ethylene-vinyl acetate copolymer, or a polyolefin elastomer of a polyolefin resin, fluorine resin or fluorine elastomer, methacrylic resin, polyphenylene oxide, modified polyphenylene ether, polyethylene terephthalate, polybutylene terephthalate, polyether ether ketone, polyamide imide, polyether imide, polyether sulfone, cyclic polyolefin, polyurethane elastomer, polyester elastomer, polyamide or polyamide elastomer, polycarbonate, polyacetal, styrene resin or styrene elastomer, and thermoplastic polyimide.

In accordance with an exemplary embodiment, the outer tube 44 is disposed radially outward of the inner tube 42 and forms the tubular structure portion 24. In addition, the outer tube 44 is formed in a hollow cylindrical shape extending linearly along the axial direction. The length of the outer tube 44 in the axial direction is formed, for example, to substantially coincide with the length of the inner tube 42 in the axial direction. In accordance with an exemplary embodiment, for example, the outer tube 44 has an outer diameter larger than that of the inner tube 42. A hollow containing unit 48 for housing the inner tube 42 is provided inside the outer tube 44. In addition, the outer tube 44 entirely covers the inner tube 42 so that the axial center of the outer tube 44 and the axial center of the inner tube 42 are close to each other and extend parallel to each other. In accordance with an exemplary embodiment, the diameter of the containing unit 48 can be set to be larger than the outer diameter of the inner tube 42 so that a space portion 50 having a predetermined volume is formed between the outer tube 44 and the inner tube 42 in a state where the inner tube 42 is contained in the containing unit.

The outer tube 44 is preferably formed of, for example, a heat-shrinkable tube. The outer tube 44 formed of the heat-shrinkable tube shrunk by heating a predetermined range of the outer tube 44 on the proximal side in a state where the shaft 20 and the inner tube 42 are disposed on the proximal side of the containing unit 48, and is tightly fixed to the shaft 20 and the inner tube 42. Accordingly, the proximal-side inner peripheral surface of the outer tube 44 in a portion positioned at the fixed region 24a is liquid-tightly fixed to the outer peripheral surfaces of the shaft 20 and the inner tube 42. For example, as shown in FIG. 3B, the outer tube 44 is heated and shrunk to be melted so as to fill in the gap between the shaft 20 and the inner tube 42. In FIG. 2, the outer diameter of the fixed portion of the outer tube 44 is smaller than the outer diameter of the unfixed portion, but the outer diameter of the outer peripheral surface of the outer tube 44 may be freely designed. For example, the outer peripheral surface of the outer tube may be formed in a tapered shape in which the outer peripheral surface of the outer tube is tapered toward the distal direction.

In accordance with an exemplary embodiment, the proximal end inclination portion 40 of the tubular structure portion 24 is formed by cutting out a portion indicated by a two-dot chain line in FIG. 2 in the fixed region 24a in a state where the inner tube 42 and the outer tube 44 are fixed to each other during the manufacturing step. Accordingly, the proximal end of the inner tube 42 and the proximal end of the outer tube 44 can be aligned to form the proximal end inclination portion 40.

In accordance with an exemplary embodiment, the outer tube 44 in the extended region 24b linearly extends the side of the inner tube 42 across the space portion 50. The space portion 50 circulates around the outer surface of the inner tube 42 along the circumferential direction and has a tubular shape extending linearly along the axial direction of the tubular structure portion 24. The space portion 50 communicates with the outlet port 36 of the shaft 20, receives a contrast agent flowing in from the outlet port 36, and makes the contrast agent flow toward the distal direction.

In accordance with an exemplary embodiment, a material that can form a heat-shrinkable tube as described above may be applied to the outer tube 44. Alternatively, the outer tube 44 may be made of the same material as the inner tube 42, and in this case, the inner tube 42 and the outer tube 44 can be firmly welded to the shaft 20 by heating the inner tube and the outer tube at the same time. In addition, the outer tube 44 may be formed to be more flexible than the inner tube 42 in order to suppress damage of blood vessels. A coating (for example, a hydrophilic coating) for smooth delivery in a blood vessel may be applied to the outer peripheral surface of the outer tube 44. The inner tube 42 or the outer tube 44 can be formed of a tube obtained by mixing the materials exemplified in the inner tube 42 or a multilayer tube in which a plurality of layers are stacked.

Figure 4A:
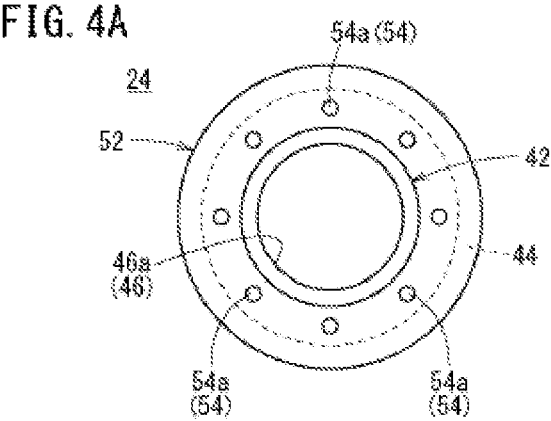
FIG. 4A is a front view of the medical elongated body of FIG. 1.

As shown in FIGS. 2 and 4A, the distal end of the outer tube 44 is interlocked with a distal tip 52 provided on the distal-side outer peripheral surface of the inner tube 42. The distal tip 52 is fixed to the distal-end outer peripheral surface of the inner tube 42 and is formed into a ring shape circulating around the distal-end outer peripheral surface. In the tubular structure portion 24, the distal end of the outer tube 44 is fixed to a proximal surface 52b of the distal tip 52, and therefore, the space portion 50 between the inner tube 42 and the outer tube 44 is closed. In addition, the outer peripheral surface of the outer tube 44 may continue to be flush with the outer peripheral surface of the distal tip 52 in a state in which the distal tip 52 is fixed to the inner tube 42 or the outer tube 44. In accordance with an exemplary embodiment, the tubular structure portion 24 may not have the distal tip 52.

The distal tip 52 has a plurality of hole portions (openings) 54 (for example, 8 hole portions in FIG. 4A) (opening portion 56) penetratingly formed in parallel to the axial direction of the distal tip 52. The plurality of hole portions 54 can be formed to have the same diameter as each other and are provided at equal intervals along the circumferential direction of the distal tip 52. In addition, each hole portion 54 has a distal opening 54a on a distal surface 52a of the distal tip 52 and a proximal opening 54b on the proximal surface 52b of the distal tip 52, and has a function of discharging a contrast agent flowing in the space portion 50. The plurality of hole portions 54 may not be formed to have the same diameter as each other. In addition, the plurality of hole portions 54 may not be provided at equal intervals along the circumferential direction of the distal tip 52.

In accordance with an exemplary embodiment, it can be preferable, for example, that the area of the opening portion 56 (the total cross-sectional area of the plurality of hole portions 54) is set to be smaller than the area of the outlet port 36 of the shaft 20 (the cross-sectional area of the lumen 26). Accordingly, it is possible to vigorously discharge a contrast agent, flowing out from the outlet port 36 to the space portion 50 and flowing inside the space portion 50, from the hole portions 54. Accordingly, when the support catheter 10 is advanced to the body lumen, the inside of a blood vessel on a distal side (including a lesion area or the like) can be favorably imaged.

The distal tip 52 is a portion mainly coming into contact with the body lumen when the support catheter 10 advances, and therefore, is preferably set to have desired physical properties. For example, the distal tip 52 is preferably formed to be more flexible than the outer tube 44 so as not to damage the body lumen. Although the material from which the distal tip 52 is fabricated not particularly limited, examples of the material include natural rubber, polyether ether ketone (PEEK), PELPRENE (registered trademark) as thermoplastic polyester elastomer, nylon, polyethylene, and polytetrafluoroethylene (PTFE).

Figure 4B:
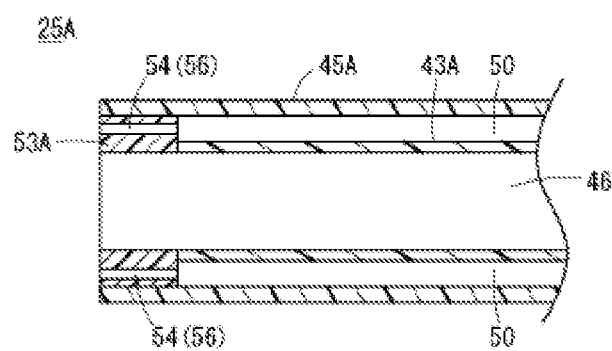
FIG. 4B is a cross-sectional side view showing a distal portion of a tubular structure portion according to a first modification example.

The configuration of the inner tube 42, the outer tube 44, and the distal chip 52 of the tubular structure portion 24 is not particularly limited. For example, as in a first modification example shown in FIG. 4B, a tubular structure portion 25A may be formed such that a distal tip 53A is fixed to the inner peripheral surface of an outer tube 45A so that the inside in the radial direction of the proximal surface of the distal tip 53A is fixed to the distal end of an inner tube 43A. Accordingly, similarly to the tubular structure portion 24 according to the present embodiment, the tubular structure portion 25A can favorably discharge a contrast agent through the hole portions 54 (opening portion 56) while blocking the distal end of the space portion 50. The configuration of the tubular structure portion 24 is not particularly limited as long as the tubular structure portion can communicate with the lumen 26, the space portion 50, and the opening portion 56 of the shaft 20 in a manner of preventing fluid leakage.

Figure 4C:
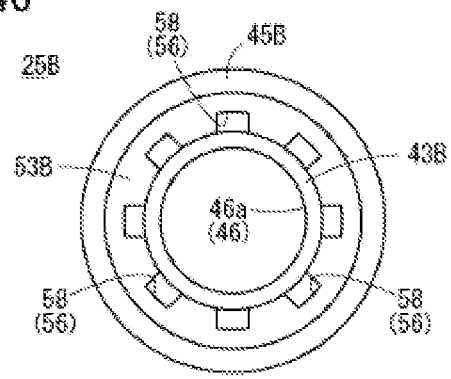
FIG. 4C is a front view showing a distal portion of a tubular structure portion according to a second modification example.

For example, as in a second modification example shown in FIG. 4C, a tubular structure portion 25B may be formed to interpose (or arrange) a distal tip 53B between an inner tube 43B and an outer tube 45B to block the distal side of the space portion 50. Furthermore, as shown in FIG. 4C, the distal tip 53B may include one or more groove portions 58 on the inner surface side or the outer surface side of the distal tip instead of the hole portions 54 as the opening portion 56 and may be configured to discharge a contrast agent through the groove portions 58. The opening portion 56 for discharging a contrast agent to the outside may be freely designed. For example, the opening portion 56 may not be provided in the distal tip 52 but may be penetratingly formed through the peripheral wall constituting the inner tube 42 or the outer tube 44.

The support catheter 10 according to the present embodiment can be configured as described above, and the actions of the support catheter 10 and effect will be described below.

For example, as shown in FIG. 5A, the support catheter 10 is selectively used when a stenosed site 102 generated in a coronary artery (blood vessel 100) is treated through percutaneous coronary intervention (PCI). In this interventional manipulation, an operator inserts and advances the guide wire 13 into the patient's aorta and inserts and delivers the guiding catheter 14 along the guide wire 13. Then, the distal end of the guiding catheter 14 is disposed at the entrance of the coronary artery.

After the distal end of the guiding catheter 14 is disposed at the entrance of the coronary artery, the operator advances the guide wire 13 (which may be replaced with a guide wire for treatment from the first guide wire) into the coronary artery and passes the guide wire through the stenosed site 102. In this state, the medical device 12 (balloon catheter) is moved through the hollow portion 16 of the guiding catheter 14 and is further advanced (or sent out) from the distal opening 16a of the guiding catheter 14. Then, the medical device 12 is guided to the stenosed site 102 along the guide wire 13.

In a case where the stenosed site 102 is formed at a position far from the entrance of the coronary artery, the distance by which the medical device 12 is advanced from the distal opening 16a becomes relatively long. As the distance becomes longer, the pushing force (advancing force) of the medical device 12 in the coronary artery becomes weaker. For example, even if it is attempted to insert the medical device 12 into the stenosed site 102, the medical device 12 cannot enter the stenosed site 102 due to occurrence of a push loss such as bending of a shaft portion 12b.

Figure 5B:
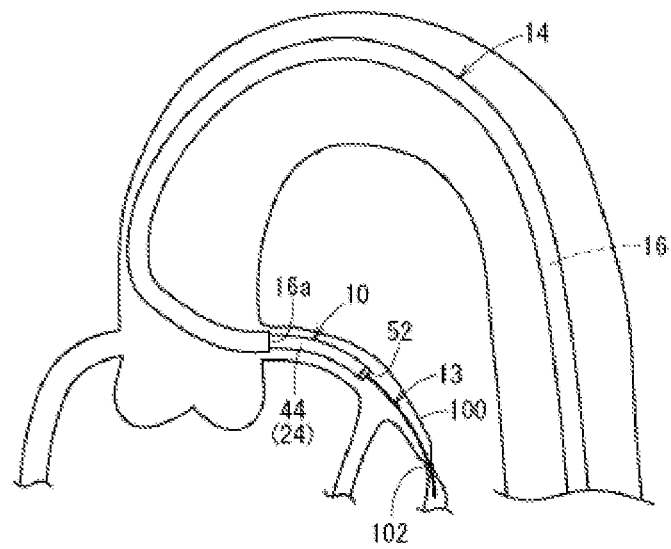
FIG. 5B is a second explanatory view showing a procedure of the manipulation continued from FIG. 5A.

In such a case, the medical device 12 is temporarily removed from the guiding catheter 14, and instead, the support catheter 10 is inserted into the guiding catheter 14. When the support catheter 10 is advanced from the distal opening 16a through the hollow portion 16, the support catheter moves in the coronary artery (blood vessel 100) along the guide wire 13 as shown in FIG. 5B.

Figure 6A:
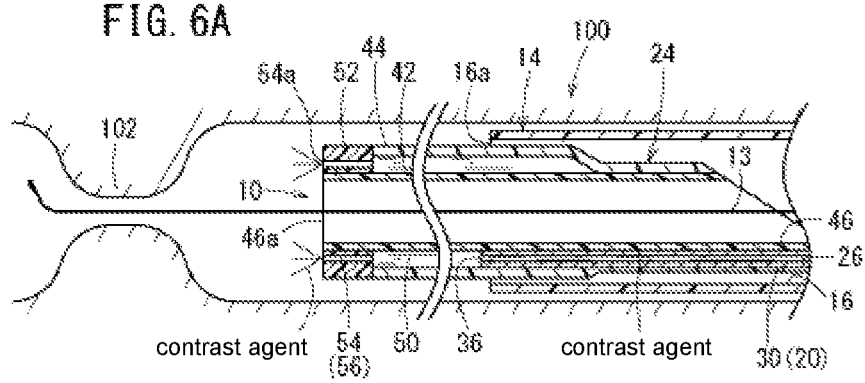
FIG. 6A is a third explanatory view showing an operation of the medical elongated body of FIG. 1 in the manipulation continued from FIG. 5B.

In a case where the operator wishes to check the state of the blood vessel 100 at the time when the support catheter 10 moves or in the proximity of the stenosed site 102, a contrast agent is discharged from the distal end of the support catheter 10 as shown in FIG. 6A. Specifically, an inflator 104 (refer to FIG. 2) for introducing a contrast agent into the support catheter 10 is connected to the hub 22 and the contrast agent is supplied from the inflator 104 to the hollow portion 22a of the hub 22. Accordingly, the contrast agent flows from the hollow portion 22a into the lumen 26 of the shaft 20 and flows through the lumen 26 which is gradually transited from the cross-sectional circular shape of the round rod portion 28 to the cross-sectional circular arc shape of the concave rod portion 30. When the contrast agent moves to the lumen 26 of the concave rod portion 30, the flow rate of the contrast agent is increased.

The contrast agent flowing to the distal end of the shaft 20 flows out from the outlet port 36 to the space portion 50 between the inner tube 42 and the outer tube 44. Here, at the proximal end of the space portion 50, the outer peripheral surface of the inner tube 42 is liquid-tightly fixed to the semicircular surface 30b of the shaft 20, the inner peripheral surface of the outer tube 44 is liquid-tightly fixed to the semicircular surface 30a of the shaft 20, and the outer peripheral surface of the inner tube 42 and the inner peripheral surface of the outer tube 44 are liquid-tightly fixed. For this reason, the contrast agent flows in the distal direction while wrapping around in a circumferential direction (i.e., the contrast agent flows turning into the space portion 50 along the circumferential direction) without leakage to the outside. Furthermore, the contrast agent flows into the plurality of hole portions 54 as the opening portion 56 of the distal tip 52 which blocks the distal end of the space portion 50, and is discharged in the distal direction from the distal opening 54*a* of each hole portion 54.

Here, the cross-sectional area of the opening portion 56 is set to be smaller than that of the lumen 26 of the concave rod portion 30 as described above. For this reason, the distal tip 52 can make it easy for the contrast agent to wrap around the distal tip 52 in the circumferential direction and can more vigorously discharge the contrast agent in the distal direction of the tubular structure portion 24 by increasing the flow rate of the contrast agent even in the hole portions 54. As a result, it is possible to image the periphery of the stenosed site 102 with a small amount of the contrast agent.

When the distal end of the support catheter 10 reaches near the stenosed site 102, the operator uses the medical device 12 again to move the medical device 12 along the support catheter 10 and the guiding catheter 14. Here, the concave groove 34 exists in the hollow portion 16 of the guiding catheter 14 along the axial direction of the shaft 20 as shown in FIG. 1. For this reason, the operator can favorably advance the medical device 12 through the hollow portion 16 and the concave groove 34.

Figure 6B:
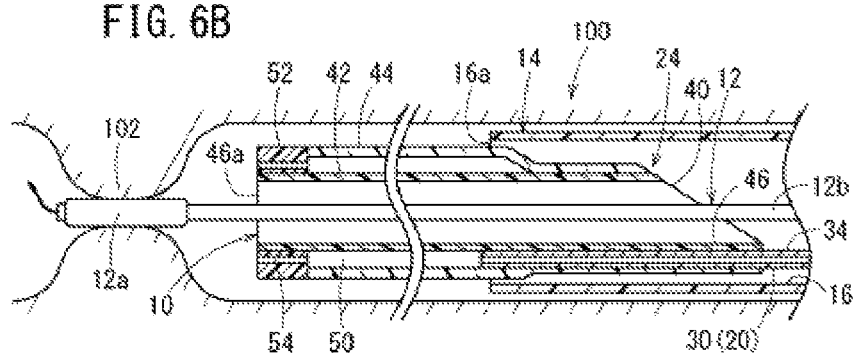
FIG. 6B is a fourth explanatory view showing an operation of the medical elongated body continued from FIG. 6A.

Furthermore, when the medical device 12 is inserted from the concave groove 34 into the insertion hole 46 of the tubular structure portion 24, the medical device advances within the insertion hole 46 and moves inside the coronary artery (blood vessel 100). The distal end of the medical device 12 is positioned in the vicinity of the stenosed site 102 in a state in which the distal end of the medical device is sent out from the distal opening 46*a* of the tubular structure portion 24. For this reason, when the operator performs an operation to push the medical device 12 into the stenosed site 102, the support catheter 10 supports the periphery of the shaft portion 12*b* and assists the pushing-in of the medical device 12. As a result, as shown in FIG. 6B, a balloon 12*a* (treatment portion) of the medical device 12 can be rather easily pushed into the stenosed site 102.

Figure 6C:
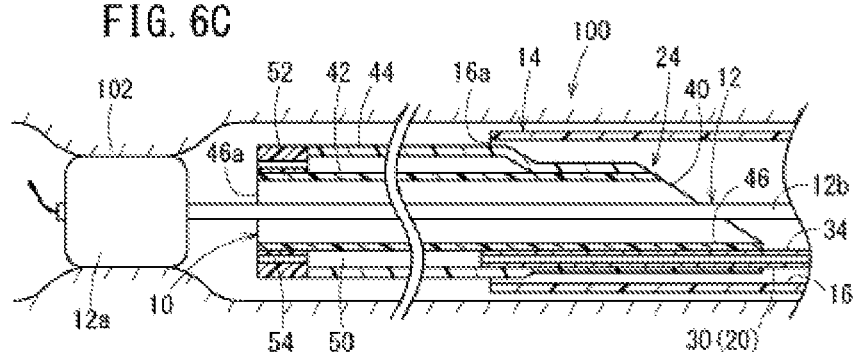
FIG. 6C is a fifth explanatory view showing an operation of the medical elongated body continued from FIG. 6B.

In a stage in which the balloon 12*a* is disposed in the stenosed site 102, the operator can favorably widen the stenosed site 102 by dilating the balloon 12*a* as shown in FIG. 6C. After dilating the balloon 12*a*, for example, the medical device 12 (balloon catheter) retreats and is removed, and the medical device 12 is changed to another medical device (stent delivery device). Another medical device can be guided to the vicinity of the stenosed site 102 using the support catheter 10 in the same manner as in the above description. Therefore, the stent in the stenosed site 102 can be indwelled.

As described above, the support catheter 10 according to the present embodiment can cause the contrast agent to flow through the lumen 26 of the shaft 20 and flow out to the space portion 50, and can further cause the contrast agent to flow in the space portion 50 and to reliably flow out from the opening portion 56 in the distal direction of the tubular structure portion 24. In accordance with an exemplary embodiment, since the proximal portion (fixed region 24*a*) of the outer tube 44 is liquid-tightly fixed to the shaft 20 and the inner tube 42 in the space portion 50 of the tubular structure portion 24, the contrast agent can be prevented from leaking outside in the middle of flowing. Accordingly, the support catheter 10 can reliably discharge the contrast agent from the distal side of the support catheter 10. In addition, the support catheter 10 can reduce the amount of the contrast agent used, and can clearly recognize (radio image) the state of the inside of the body with the contrast agent flowing to a more distal side than the tubular structure portion 24.

In addition, the support catheter 10 has the concave groove 34 on the distal side of the shaft 20, and therefore, the space on the proximal side of the tubular structure portion 24 is widened. For this reason, when the medical device 12 is inserted toward the tubular structure portion 24, the support catheter 10 can suppress the medical device 12 from being caught by the tubular structure portion 24, and can smoothly insert the medical device 12 into the insertion hole 46. In addition, by making the cross-sectional area of the lumen 26 of the shaft 20 at the distal portion be smaller than that of the lumen 26 of the shaft 20 at the proximal portion, the flow speed of the contrast agent from the proximal side of the shaft 20 to the distal side of the shaft 20 can be increased when the contrast agent flows the lumen 26 of the shaft 20. Accordingly, the support catheter 10 can make a highly viscous fluid such as a contrast agent flow rather smoothly. In addition, since the support catheter 10 includes the groove portion 34 on the outer surface of the shaft 20, the medical device 12 can follow the groove portion 34 and the medical device 12 slides smoothly.

Furthermore, since the lumen 26 of the shaft 20 at the distal portion is formed in a U-shape, the support catheter 10 can secure the lumen 26 of the shaft 20 widely (i.e., a cross-sectional area of the lumen 26 is relatively large) at a joint portion between the shaft 20 and the tubular structure portion 24. Accordingly, the operator can cause a contrast agent to smoothly flow from a proximal side (hand-side) of the shaft 20 to the opening portion 56 of the tubular structure portion 24 through the lumen 26 of the shaft 20 and the space portion 50 of the tubular structure portion 24. In addition, since the lumen 26 of the shaft 20 at the distal portion is formed in a U-shape, the support catheter 10 can widen the space (i.e., increase an inner diameter or area) on the proximal side of the tubular structure portion 24 through which the medical device 12 is to be inserted. Accordingly, the operator can smoothly insert the medical device 12 into the insertion hole 46 of the tubular structure portion 24.

Since the inner tube 42 is fixed to the concave groove 34, the inner tube 42 can be firmly fixed to the concave groove. For this reason, in the support catheter 10, the joining between the tubular structure portion 24 and the shaft 20 can be enhanced, and therefore, a risk of rupture of the tubular structure portion 24 and the shaft 20 can be suppressed.

Since the cross-sectional area of the opening portion 56 of the support catheter 10 is made to be smaller than that of the lumen 26 of the shaft 20 on the distal side, a fluid flowing from the lumen 26 of the shaft 20 can be smoothly discharged. Accordingly, the support catheter 10 can make a highly viscous fluid such as a contrast agent flow smoothly toward the opening portion 56.

In addition, since the tubular structure portion 24 includes the flexible distal tip 52, damage of the blood vessel 100 can be suppressed due to the distal portion of the support catheter 10 when the support catheter advances within the blood vessel 100.

The support catheter 10 according to the present invention is not limited to the above-described configuration, and various modification examples and application examples can be applied. For example, the cross-sectional shape of the lumen 26 of the shaft 20 may be not only formed in an arc shape corresponding to the concave rod portion 30, and various configurations may be employed.

In addition, a fluid discharged from the support catheter 10 is not limited to the contrast agent, and a configuration so as to make various fluids applied in the interventional manipulation flow out can be employed. Examples of the fluids include a saline solution, an embolic agent, and various drug solutions used for treatment. The opening portion 56 of the support catheter 10 may be appropriately modified in accordance with the viscosity of a fluid. For example, a configuration in which the opening portion 56 is open over the whole circumference in the circumferential direction of the tubular structure portion 24 without including the distal tip 52.

In addition, a support catheter 70 (medical elongated body 70) according to another application example shown in FIG. 7 is different from the support catheter 10 according to the present embodiment from the viewpoint that a reinforcement line 76 (reinforcement body) for reinforcing a tubular structure portion 72 is provided on the outer peripheral surface of an inner tube 74 of the tubular structure portion 72 constituting the space portion 50. The reinforcement line 76 is formed as a coil that spirally wound around the outer peripheral surface of the inner tube 74. The material from which the reinforcement line 76 is fabricated in not particularly limited, and a metallic material (such as a metal blade) or a resin material (such as a nylon blade) may be appropriately applied.

When a contrast agent introduced from the shaft 20 flows in the distal direction using the reinforcement line 76, the contrast agent flows in the space portion 50 along the unevenness of the spiral shape to thoroughly spread the contrast agent in the circumferential direction of the space portion 50. That is, the reinforcement line 76 provided in the inner tube 42 can stably maintain the extended state of the tubular structure portion 72 and can stir the contrast agent at the same time.

In the support catheter 10, the configuration of diffusing a contrast agent may be freely designed. For example, the reinforcement line 76 may be provided on the inner peripheral surface of the outer tube 44. In addition, the shape of the reinforcement line 76 is not limited to the spiral shape. For example, a mesh-shaped reinforcement line may be provided on a part or the whole of the wall surface constituting the space portion 50, or one or more ring-shaped reinforcement lines circulating around the space portion 50 may be provided. For example, the support catheter 10 may have a configuration in which the space portion 50 is secured by protrusively forming one or more projections (not shown in the drawing) from the outer peripheral surface of the inner tube 42 or the inner peripheral surface of the outer tube 44 to support the other surface. The projections can also stir the contrast agent flowing into the space portion 50.

The present invention is not limited to the above-described embodiment. For example, the present invention can be variously modified within the scope not departing from the gist of the present invention. For example, the support catheter 10 may have a configuration as a microcatheter for reinforcing the guide wire 13 to support the guide wire's 13 movement in a case where it is difficult for the guide wire 13 to pass through the stenosed site 102 when the guide wire 13 is advanced within the blood vessel 100, by variously modifying the present invention.

The detailed description above describes a medical elongated body used in an interventional manipulation, for example, for assisting advancement of a medical device. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A medical elongated body, the medical elongated body comprising:
    a shaft having a lumen through which a fluid can flow;
    a hub interlocked and fixed to a proximal side of the shaft; and
    a cylindrical structure portion which is provided at a distal portion of the shaft and wherein a proximal-most end of the cylindrical structure portion is located distally of the proximal side of the shaft, the cylindrical structure portion including an insertion hole extending in an axial direction from a proximal end to a distal end of the cylindrical structure portion, the insertion hole including a proximal opening at the proximal end of the cylindrical structure portion and a distal opening at the distal end of the cylindrical structure portion, wherein the cylindrical structure portion includes:
        a first cylindrical body which includes the insertion hole and is fixed to the distal portion of the shaft;
        a second cylindrical body which is disposed radially outward of the first cylindrical body and is liquid-tightly fixed to the distal portion of the shaft and a proximal portion of the first cylindrical body;
        a space portion which is provided between the first cylindrical body and the second cylindrical body and communicates with the lumen of the shaft; and
        an opening portion which is positioned at a distal portion of the cylindrical structure portion and through which the fluid flowing from the lumen of the shaft into the space portion flows out of the cylindrical structure portion.

2. The medical elongated body according to claim 1, wherein the shaft has, on a distal side of the shaft, a groove portion formed by recessing an outer surface of the shaft toward the lumen of the shaft, the groove portion forming most of the shaft in the axial direction, and a cross-sectional area of the lumen of the shaft at the distal portion in a cross-section orthogonal to an axial center of the shaft is smaller than that of the lumen of the shaft at a proximal portion in a cross-section orthogonal to the axial center of the shaft.

3. The medical elongated body according to claim 2, wherein the first cylindrical body is fixed to the groove portion of the shaft.

4. The medical elongated body according to claim 1, wherein the lumen of the shaft at the distal portion in a cross-section orthogonal to an axial center of the shaft is formed in a U-shape.

5. The medical elongated body according to claim 1, wherein a cross-sectional area of the opening portion in a cross-section orthogonal to an axial center of the shaft is smaller than that of the lumen of the shaft at the distal portion in a cross-section orthogonal to the axial center of the shaft.

6. The medical elongated body according to claim 1, wherein the cylindrical structure portion has a distal tip, the distal tip being made of a material more flexible than that of the second cylindrical body, and the distal tip being configured to fix the first cylindrical body and the second cylindrical body at a distal side of the cylindrical structure portion while forming the opening portion.

7. The medical elongated body according to claim 1, wherein at least one of an outer surface of the first cylindrical body and an inner surface of the second cylindrical body is provided with a reinforcement body for reinforcing the cylindrical structure portion.

8. The medical elongated body according to claim 1, further comprising:
a distal tip arranged on a distal end of the cylindrical structure portion, the distal tip having a plurality of openings arranged in parallel to an axial direction of the distal tip and configured to discharge a contrast agent flowing in the space portion.

9. The medical elongated body according to claim 8, wherein the plurality of openings is arranged at equal intervals along a circumferential direction of the distal tip.

10. The medical elongated body according to claim 9, wherein each of the plurality of openings has a same diameter, and the each of the plurality of openings having a distal opening on a distal surface of the distal tip and a proximal opening on a proximal surface of the distal tip; and
a total cross-sectional area of the plurality of openings is less than a total cross-sectional area of an outlet port of the lumen of the shaft.

11. The medical elongated body according to claim 1, further comprising:
a distal tip configured to be fixed to an inner peripheral surface of the second cylindrical body, and wherein a proximal surface of the distal tip is fixed to a distal end of the first cylindrical body; and
a distal portion of the second cylindrical body has a constant outer diameter.

12. The medical elongated body according to claim 11, wherein the distal tip includes one or more groove portions on an inner surface side or an outer surface side of the distal tip, the one or more grooves being configured to discharge a contrast agent through the one or more groove portions.

13. A medical elongated body, the medical elongated body comprising:
a shaft having a lumen through which a fluid can flow; and
a cylindrical structure portion arranged at a distal portion of the shaft, the cylindrical structure portion including:
an inner cylindrical body configured to be fixed to the distal portion of the shaft, the inner cylindrical body includes a lumen extending in an axial direction from a proximal end to a distal end of the inner cylindrical body, the inner cylindrical body including a proximal opening at the proximal end of the inner cylindrical body and a distal opening at the distal end of the inner cylindrical body, the inner cylindrical body being fixed directly to an outer surface of the shaft, and wherein the lumen of the inner cylindrical body is parallel with the lumen of the shaft at the distal portion of the shaft;
an outer cylindrical body radially disposed outward of the inner cylindrical body and is liquid-tightly fixed to the distal portion of the shaft and a proximal portion of the inner cylindrical body;
an annular space provided between the inner cylindrical body and the outer cylindrical body and in fluid communication with the lumen of the shaft;
a distal tip positioned at a distal portion of the cylindrical structure portion and through which the fluid flowing from the lumen of the shaft is discharged into a body lumen from the annular space; and
a proximal end inclination portion, which is inclined obliquely with respect to the axial direction of the cylindrical structure portion, and wherein the proximal end inclination portion is provided on the proximal end of the cylindrical structure portion.

14. The medical elongated body according to claim 13, wherein the shaft has, on a distal side of the shaft, a groove portion formed by recessing an outer surface of the shaft toward the lumen of the shaft, the groove portion forming most of the shaft in the axial direction.

15. The medical elongated body according to claim 14, wherein a cross-sectional area of the lumen of the shaft at the distal portion in a cross-section orthogonal to an axial center of the shaft is smaller than that of the lumen of the shaft at a proximal portion in a cross-section orthogonal to the axial center of the shaft.

16. The medical elongated body according to claim 13, wherein the lumen of the shaft at the distal portion in a cross-section orthogonal to an axial center of the shaft is formed in a U-shape.

17. A method for discharging a contrast agent into a body lumen, the method comprising: inserting a medical elongated body into the body lumen, the medical elongated body including a shaft having a lumen through which the contrast agent can flow, a hub interlocked and fixed to a proximal side of the shaft, and a cylindrical structure portion which is provided at a distal portion of the shaft and wherein a proximal-most end of the cylindrical structure portion is located distally of the proximal side of the shaft, the cylindrical structure portion including an insertion hole extending in an axial direction from a proximal end to a distal end of the cylindrical structure portion, the insertion hole including a proximal opening at the proximal end of the cylindrical structure portion and a distal opening at the distal end of the cylindrical structure portion, wherein the cylindrical structure portion includes: a first cylindrical body which has the insertion hole and is fixed to the distal portion of the shaft; a second cylindrical body which is disposed radially outward of the first cylindrical body and is liquid-tightly fixed to the distal portion of the shaft and a proximal portion of the cylindrical tubular body; a space portion which is provided between the first cylindrical body and the second cylindrical body and communicates with the lumen of the shaft; and an opening portion which is positioned at a distal portion of the cylindrical structure portion; and discharging the contrast agent through the opening portion into the body lumen.

18. The method according to claim 17, comprising: recessing an outer surface of the shaft toward the lumen of the shaft on a distal side of the shaft, and a cross-sectional area of the lumen of the shaft at the distal portion in a cross-section orthogonal to an axial center of the shaft is smaller than that of the lumen of the shaft at a proximal portion in a cross-section orthogonal to the axial center of the shaft.

19. The method according to claim 17, comprising:
arranging a distal tip on a distal portion of the cylindrical structure portion, the distal tip being made of a material more flexible than that of the second cylindrical body, the distal tip being configured to fix the first cylindrical body and the cylindrical body at a distal side of the cylindrical structure portion while forming the opening portion.

20. The method according to claim 17, comprising:
advancing a medical device into the body lumen through a distal opening of the insertion hole of the cylindrical structure portion.

* * * * *